(12) United States Patent    (10) Patent No.: US 11,479,754 B2
Nakamura et al.                  (45) Date of Patent:     Oct. 25, 2022

(54) METHOD FOR PRODUCING CULTIVATED EPITHELIAL CELL SHEET

(71) Applicants: KYOTO PREFECTURAL PUBLIC UNIVERSITY CORPORATION, Kyoto (JP); Foundation for Biomedical Research and Innovation at Kobe, Hyogo (JP)

(72) Inventors: Takahiro Nakamura, Kyoto (JP); Shigeru Kinoshita, Kyoto (JP); Seiichi Yokoo, Tokyo (JP); Satoru Yamagami, Tokyo (JP)

(73) Assignees: KYOTO PREFECTURAL PUBLIC UNIVERSITY CORPORATION, Kyoto (JP); FOUNDATION FOR BIOMEDICAL RESEARCH AND INNOVATION AT KOBE, Hyogo (JP)

( * ) Notice: Subject to any disclaimer, the term of this patent is extended or adjusted under 35 U.S.C. 154(b) by 1022 days.

(21) Appl. No.: 16/095,173

(22) PCT Filed: Apr. 19, 2017

(86) PCT No.: PCT/JP2017/015704
§ 371 (c)(1),
(2) Date: Oct. 19, 2018

(87) PCT Pub. No.: WO2017/183655
PCT Pub. Date: Oct. 26, 2017

(65) Prior Publication Data
US 2019/0169571 A1    Jun. 6, 2019

(30) Foreign Application Priority Data

Apr. 20, 2016  (JP) .............................. JP2016-084471

(51) Int. Cl.
*C12N 5/071* (2010.01)
*A61L 27/36* (2006.01)
*A61K 35/38* (2015.01)
*A61K 35/36* (2015.01)
*A61L 27/00* (2006.01)

(52) U.S. Cl.
CPC ............ *C12N 5/0632* (2013.01); *A61K 35/38* (2013.01); *A61L 27/3604* (2013.01); *A61L 27/3641* (2013.01); *C12N 5/0625* (2013.01); *A61K 35/36* (2013.01); *A61L 27/00* (2013.01); *C12N 2500/00* (2013.01); *C12N 2500/30* (2013.01); *C12N 2500/34* (2013.01); *C12N 2500/35* (2013.01); *C12N 2500/90* (2013.01); *C12N 2501/11* (2013.01); *C12N 2501/117* (2013.01); *C12N 2501/39* (2013.01); *C12N 2501/727* (2013.01); *C12N 2501/90* (2013.01); *C12N 2533/92* (2013.01)

(58) Field of Classification Search
None
See application file for complete search history.

(56) References Cited

U.S. PATENT DOCUMENTS

| 5,906,937 | A | 5/1999 | Sugiyama et al. |
|---|---|---|---|
| 6,043,089 | A | 3/2000 | Sugiyama et al. |
| 6,057,148 | A | 5/2000 | Sugiyama et al. |
| 7,959,939 | B2 | 6/2011 | Yamagami et al. |
| 2007/0238173 | A1 | 10/2007 | Yamagami et al. |
| 2008/0026030 | A1 | 1/2008 | Kinoshita et al. |
| 2010/0184221 | A1 | 7/2010 | Yokoo et al. |
| 2012/0282318 | A1 | 11/2012 | Nishida et al. |
| 2016/0264936 | A1 | 9/2016 | Nakano et al. |
| 2016/0266114 | A1 | 9/2016 | Koizumi et al. |
| 2017/0319748 | A1 | 11/2017 | Kuwahara et al. |
| 2018/0010093 | A1* | 1/2018 | Nishida ............... C12N 5/0621 |

FOREIGN PATENT DOCUMENTS

| EP | 2 975 117 | 1/2016 |
|---|---|---|
| JP | 8-243156 | 9/1996 |
| JP | 2005-229869 | 9/2005 |
| JP | 2010-22327 | 2/2010 |
| JP | 2010-46058 | 3/2010 |
| JP | 2015-155400 | 8/2015 |
| WO | 2006/003 818 | 1/2006 |
| WO | 2009/011139 | 1/2009 |
| WO | 2011/021706 | 2/2011 |
| WO | 2012/022725 | 2/2012 |
| WO | 2014/159356 | 10/2014 |
| WO | 2015/016371 | 2/2015 |
| WO | 2015/068505 | 5/2015 |
| WO | 2015/107738 | 7/2015 |

OTHER PUBLICATIONS

International Search Report dated Jun. 20, 2017 in International (PCT) Application No. PCT/JP2017/015704.
Kinoshita et al., "Development of Cultivated Mucosal Epithelial Sheet Transplantation for Ocular Surface Reconstruction", Artificial Organs, vol. 28, No. 1, 2004, pp. 22-27.
Yokoo et al., "Human Corneal Epithelial Equivalents for Ocular Surface Reconsuuction in a Complete Serum-Free Culture System without Unknown Factors", Investigative Ophthalmology & Visual Science, vol. 49, No. 6, 2008, pp. 2438-2443.
Miyashita et al., "Long-Term Maintenance of Limbal Epithelial Progenitor Cells Using Rho Kinase Inhibitor and Keratinocyte Growth Factor", Stem Cells Translational Medicine, vol. 2, 2013, pp. 758-765.
Nakamura et al., "The Successful Culture and Autologous Transplantation of Rabbit Oral Mucosal Epithelial Cells on Amniotic Membrane", Investigative Ophthalmology & Visual Science, vol. 44, No. 1, Jan. 2003, pp. 106-116.

(Continued)

*Primary Examiner* — Allison M Fox
(74) *Attorney, Agent, or Firm* — Wenderoth, Lind & Ponack, L.L.P.

(57) ABSTRACT

A method for producing an epithelial cell sheet, comprising culturing cells derived from oral mucosal epithelial cells on a substrate in a serum-free medium, wherein the serum-free medium comprises (i) EGF protein or KGF protein, (ii) B-27 supplement, and (iii) a ROCK inhibitor.

2 Claims, 12 Drawing Sheets

Specification includes a Sequence Listing.

(56) References Cited

OTHER PUBLICATIONS

Nakamura et al., "Long-term results of autologous cultivated oral mucosal epithelial transplantation in the scar phase of severe ocular surface disorders", Br. J. Ophthalmol, vol. 95, 2011, pp. 942-946.

Nakamura et al., "Transplantation of cultivated autologous oral mucosal epithelial cells in patients with severe ocular surface disorders", Br. J. Ophthalmol, vol. 88, 2004, pp. 1280-1284.

Koizumi et al., "Cultivation of Corneal Epithelial Cells on Intact and Denuded Human Amniotic Membrane", Investigative Ophthalmology & Visual Science, vol. 41, No. 9, Aug. 2000, pp. 2506-2513.

Barrandon et al., "Three clonal types of keratinocyte with different capacities for multiplication", Proc. Natl. Acad. Sci., vol. 84, Apr. 1987, pp. 2303-2306.

Ilmarinen et al., "Towards a defined, serum- and feed-free culture of stratified human oral mucosal epithelium for ocular surface reconstruction", Acta Ophthalmol., vol. 91, 2013, pp. 744-750.

Yokoo et al. "Progress in Corneal Epithelial Culture", Japanese Journal of Clinical Ophthalmology, vol. 66, No. 11, 2012, 7 pages, with English abstract.

Extended European Search Report dated Oct. 10, 2019 in corresponding European Patent Application No. 17785993.1.

Nakamura et al., "Development of functional human oral mucosal epithelial stem/progenitor cell sheets using a feeder-free and serum-free culture system for ocular surface reconstruction", Scientific Reports, vol. 6, No. 1, DOI:10.1038/srep37173, 2016.

Utheim, "Concise Review: Transplantation of Cultured Oral Mucosal Epithelial Cells for Treating Limbal Stem Cell Deficiency—Current Status and Future Perspectives", Stem Cells, vol. 33, No. 6, pp. 1685-1695, 2015.

Kobayashi et al., "Ocular Surface Reconstruction With a Tissue-Engineered Nasal Mucosal Epithelial Cell Sheet for the Treatment of Severe Ocular Surface Diseases", Stem Cells Translational Medicine, vol. 4, No. 1, pp. 99-109, 2014.

Liu et al., "Modern Practical Histology and Tissue Chemical Technology", Hubei Science and Technology Press, 2003. p. 48, with English Translation and Cited in reference "CC".

Peng, Q., "Ophthalmology of Integrated Traditional Chinese and Western Medicine" China Traditional Chinese Medicine Press, 2010, p. 307, with English Translation and Cited in reference "CC".

Office Action dated Feb. 25, 2022 in corresponding Chinese Patent Application No. 201780037143.1, with English Translation.

Communication pursuant to Article 94(3) EPC dated Mar. 4, 2022 in corresponding European Patent Application No. 17 785 993.1.

\* cited by examiner

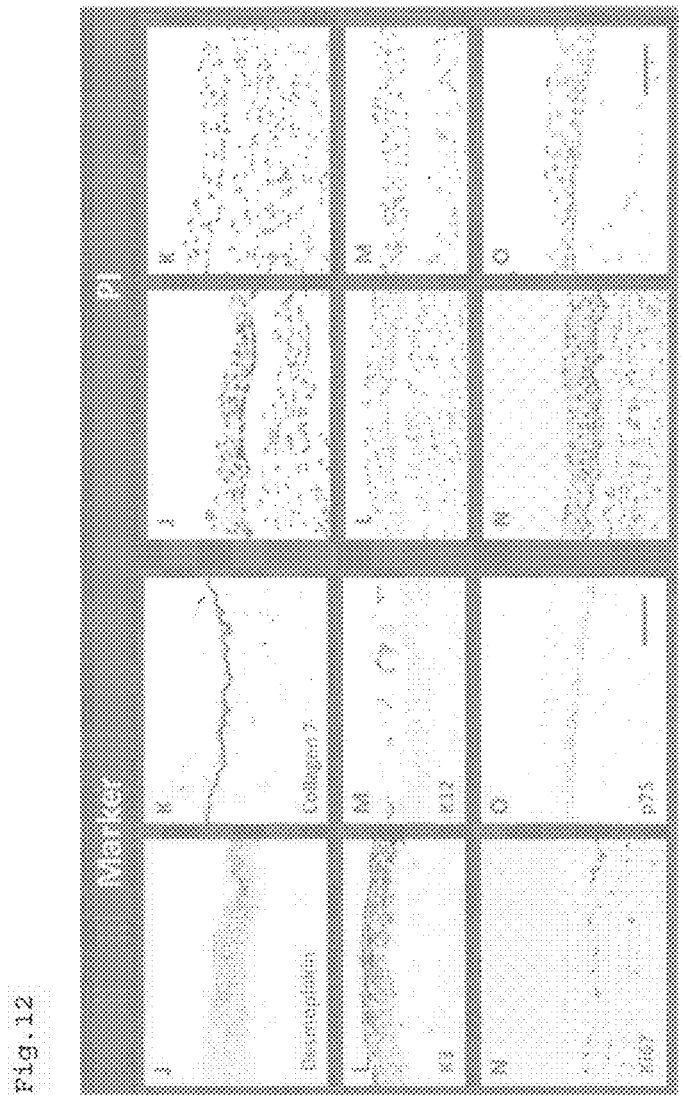

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: human K12 F

<400> SEQUENCE: 1
```
aatcatgggg cagatcttgt                                               20

<210> SEQ ID NO 2
<211> LENGTH: 20
<212> TYPE: DNA
<213> ORGANISM: Artificial Sequence
<220> FEATURE:
<223> OTHER INFORMATION: human K12 R

<400> SEQUENCE: 2
aaggtgatgg tttggaggaa                                               20

<210> SEQ ID NO 3
<211> LENGTH: 19
<212> TYPE: DNA
<213> ORGANISM: Artificial Sequence
<220> FEATURE:
<223> OTHER INFORMATION: human K3 F

<400> SEQUENCE: 3
ggcagagatc gagggtgtc                                                19

<210> SEQ ID NO 4
<211> LENGTH: 21
<212> TYPE: DNA
<213> ORGANISM: Artificial Sequence
<220> FEATURE:
<223> OTHER INFORMATION: human K3 R

<400> SEQUENCE: 4
gtcatccttc gcctgctgta g                                             21

<210> SEQ ID NO 5
<211> LENGTH: 20
<212> TYPE: DNA
<213> ORGANISM: Artificial Sequence
<220> FEATURE:
<223> OTHER INFORMATION: human ALDH3 F

<400> SEQUENCE: 5
ttgcagagac atccagtggt                                               20

<210> SEQ ID NO 6
<211> LENGTH: 20
<212> TYPE: DNA
<213> ORGANISM: Artificial Sequence
<220> FEATURE:
<223> OTHER INFORMATION: human ALDH3 R

<400> SEQUENCE: 6
ttggtctaga aagggtgga                                                20

<210> SEQ ID NO 7
<211> LENGTH: 18
<212> TYPE: DNA
<213> ORGANISM: Artificial Sequence
<220> FEATURE:
<223> OTHER INFORMATION: human TKT F

<400> SEQUENCE: 7
ctgcttcatc cggaccag                                                 18

<210> SEQ ID NO 8
<211> LENGTH: 20
<212> TYPE: DNA
<213> ORGANISM: Artificial Sequence

```
<220> FEATURE:
<223> OTHER INFORMATION: human TKT R

<400> SEQUENCE: 8
cacacttcat acccgcccta                                          20

<210> SEQ ID NO 9
<211> LENGTH: 21
<212> TYPE: DNA
<213> ORGANISM: Artificial Sequence
<220> FEATURE:
<223> OTHER INFORMATION: human p75 F

<400> SEQUENCE: 9
tgagtgctgc aaagcctgca a                                        21

<210> SEQ ID NO 10
<211> LENGTH: 21
<212> TYPE: DNA
<213> ORGANISM: Artificial Sequence
<220> FEATURE:
<223> OTHER INFORMATION: human p75 R

<400> SEQUENCE: 10
tctcatcctg gtagtagccg t                                        21

<210> SEQ ID NO 11
<211> LENGTH: 20
<212> TYPE: DNA
<213> ORGANISM: Artificial Sequence
<220> FEATURE:
<223> OTHER INFORMATION: human beta-actin F

<400> SEQUENCE: 11
ggacttcgag caagagatgg                                          20

<210> SEQ ID NO 12
<211> LENGTH: 20
<212> TYPE: DNA
<213> ORGANISM: Artificial Sequence
<220> FEATURE:
<223> OTHER INFORMATION: human beta-actin R

<400> SEQUENCE: 12
atctgctgga aggtggacag                                          20
```

METHOD FOR PRODUCING CULTIVATED EPITHELIAL CELL SHEET

TECHNICAL FIELD

The present invention mainly relates to a method for producing a cultivated epithelial sheet.

BACKGROUND ART

Methods for producing a cultivated epithelial sheet (cultivated oral mucosal epithelial cell sheet (COMECS)) for use in corneal regenerative medicine have been reported (Patent Literature 1 and Non-patent Literature 1 to 3). Cultivated epithelial sheets obtained by the methods are used in the treatment of intractable keratoconjunctival disease and have good treatment results. In Japan, autologous cultivated oral mucosal epithelial sheet transplantation (COMET) is being conducted as advanced medical treatment.

CITATION LIST

Patent Literature

PTL 1: WO2006/003818

Non-Patent Literature

NPL 1: Nakamura T, Endo K, Cooper L J et al. Investigative Ophthalmology & Visual Science, 2003; 44:106-116.
NPL 2: Nakamura T, Inatomi T, Sotozono C et al. The British Journal of Ophthalmology, 2004; 88:1280-1284.
NPL 3: Nakamura T, Takeda K, Inatomi T et al. The British Journal of Ophthalmology, 2011; 95:942-946.

SUMMARY OF INVENTION

Technical Problem

Conventionally known methods for producing cultivated epithelium require the use of 3T3 feeder cells derived from mice and fetal bovine serum. However, from the viewpoint of safety and ethical considerations, it is necessary to remove xenogeneic materials from the culture system. Therefore, the present inventors attempted to develop a culture method (culture technique) that does not require the use of feeder cells or serum.

Solution to Problem

The present inventors conducted extensive research to solve the above problem, and, surprisingly, found that the problem can be solved by using a serum-free medium comprising (i) EGF protein or KGF protein, (ii) B-27 supplement, and (iii) a ROCK inhibitor. The present invention has been accomplished by further conducting research based on this finding.

Specifically, the present invention includes the following embodiments.

Item 1. A method for producing an epithelial cell sheet, the method comprising culturing cells derived from oral mucosal epithelial cells on a substrate in a serum-free medium, wherein the serum-free medium comprises
(i) EGF protein or KGF protein,
(ii) B-27 supplement, and
(iii) a ROCK inhibitor.

Item 2. The method according to item 1, wherein the medium further comprises at least one member selected from the group consisting of
(iv) polysaccharides,
(v) catechins, and
(vi) corticoids.

Item 3. An epithelial cell sheet obtained by the method according to items 1 or 2.

Item 4. A serum-free medium for producing an epithelial cell sheet using cells derived from oral mucosal epithelial cells, the medium comprising
(i) EGF protein or KGF protein,
(ii) B-27 supplement, and
(iii) a ROCK inhibitor.

Advantageous Effects of Invention

The present invention provides a culture method that does not require the use of feeder cells or serum. A cultivated epithelial sheet provided by the present invention has excellent properties for use in the treatment of intractable keratoconjunctival disease. Therefore, the present invention can further improve the treatment techniques for intractable keratoconjunctival disease.

BRIEF DESCRIPTION OF DRAWINGS

FIG. 8 separately shows antibody stain images (marker) and nuclear stain images (propidium iodide (PI)).

FIG. 9 separately shows antibody stain images and nuclear stain images (propidium iodide (PI)) of K12.

FIG. 10 separately shows antibody stain images and nuclear stain images (propidium iodide (PI)) of p75.

FIG. 12 shows black and white inverted images of FIG. 6J-O. FIG. 12 separately shows antibody stain images (marker) and nuclear stain images (propidium iodide (PI)).

DESCRIPTION OF EMBODIMENTS

Figure 1:
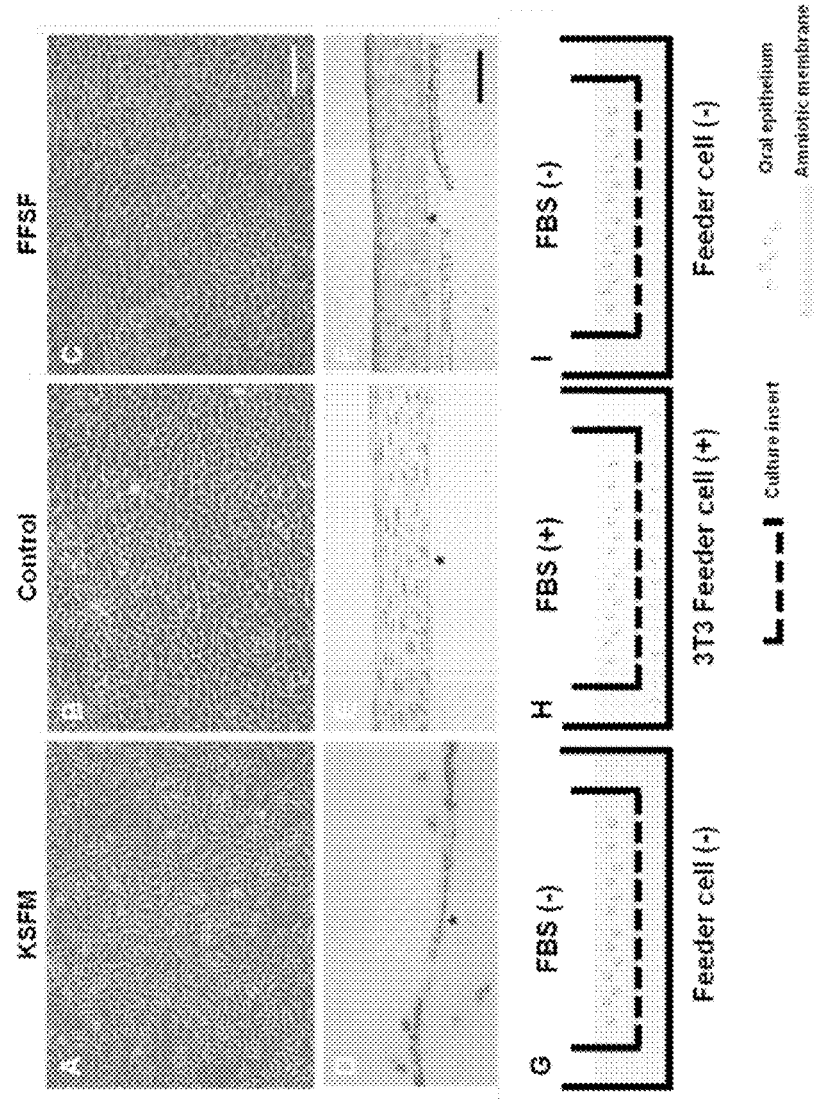
FIG. 1 shows phase-contrast microscope images and results of histological examination of cultivated oral mucosal epithelial cell sheets (COMECSs). (A-C): phase-contrast microscope images on day 7 of culture; (D-F): bright-field microscope images of cross-sections of COMECSs stained with hematoxylin and eosin (HE) (the asterisks indicate a denuded amniotic membrane); and (G-I): schematic diagrams of culture conditions. Bar: 100 μm.

The serum-free medium of the present invention comprises
(i) EGF protein or KGF protein,
(ii) B-27 supplement, and
(iii) a ROCK inhibitor.

As the basal medium of the serum-free medium used in the present invention, a known serum-free medium, in particular, a serum-free medium for culture of stem cells, can be used. Specific examples include Minimum Essential Medium (MEM), Dulbecco's Modified Eagle's Medium (DMEM), Ham's F12 medium, Basal Medium Eagle (BME), Iscove's Modified Dulbecco's Medium (IMDM), Roswell Park Memorial Institute medium (RPMI medium), Defined Keratinocyte Serum Free Medium (Defined Keratinocyte-SFM) and the like, and mixtures thereof.

The EGF (epidermal growth factor) protein and KGF (keratinocyte growth factor) protein, which are growth factors, are both known proteins. From the viewpoint of avoiding the use of xenogeneic materials, the EGF protein or KGF protein is preferably derived from a human. As the EGF protein or KGF protein, a recombinant protein can be used.

The amount of the EGF (epidermal growth factor) protein or the KGF (keratinocyte growth factor) protein may be about 1 to 100 ng/ml, preferably about 2 to 50 ng/ml, and more preferably about 5 to 20 ng/ml in the final concentration.

The B-27 (trademark) supplement is a known serum-free supplement, and a commercially available product can be used. The B-27 supplement is known, as its application, for example, to be added in a medium used for culturing and maintaining nerve cells. The B-27 supplement contains biotin, L-carnitine, corticosterone, ethanolamine, D(+) galactose, reduced glutathione, linoleic acid, linolenic acid, progesterone, putrescine, retinyl acetate, selenium, triiodo-L-thyronine, vitamin E, vitamin E acetate, bovine albumin, catalase, insulin, superoxide dismutase, and transferrin.

The amount of the B-27 (trademark) supplement may be about 0.2 to 20% (w/v), preferably about 0.5 to 10% (w/v), and more preferably about 1 to 5% (w/v) in the final concentration.

The ROCK inhibitor is not particularly limited as long as it is a compound that specifically inhibits the function of Rho-associated kinase (ROCK). Examples include Y27632 ((R)-(+)-trans-N-(4-pyridyl)-4-(1-aminoethyl)-cyclohexan-ecarboxamide), Y39983 ((R)-(+)-N-(4-1H-pyrrolo [2,3-b] pyridin-yl)-4-(1-aminoethyl)-benzamide), fasudil hydrochloride (1-(5-Isoquinolinesulfonyl) homopiperazine Hydrochloride), and the like.

The amount of the ROCK inhibitor may be about 1 to 100 μM/L, preferably about 2 to 50 μM/L, and more preferably about 5 to 20 μM/L in the final concentration.

The serum-free medium of the present invention may further contain one or more catechins. Examples of catechins include catechin, epicatechin, gallocatechin, epigallocatechin, epicatechin gallate, epigallocatechin gallate, and the like. Of these, epigallocatechin gallate is preferable. The amount of the catechin may be about 0.5 to 100 mg/ml, preferably about 1 to 50 mg/ml, and more preferably about 2 to 20 mg/ml in the final concentration.

The serum-free medium of the present invention may further contain one or more polysaccharides. Examples of polysaccharides include dextran, cellulose, mannan, starch, agarose, and the like. Of these, dextran (e.g., Dextran 40, which has an average molecular weight of about 40,000) is preferable. The amount of the polysaccharide may be about 0.1 to 20% (w/v), preferably about 0.2 to 10% (w/v), and about 0.5 to 5% (w/v) in the final concentration.

The serum-free medium of the present invention may further contain one or more corticoids. Examples of corticoids include cortisone, hydrocortisone, corticosterone, and the like. Of these, hydrocortisone is preferable. The amount of the corticoid may be about 0.01 to 5% (w/v), preferably about 0.05 to 2% (w/v), and about 0.1 to 1% (w/v) in the final concentration.

The serum-free medium of the present invention may contain any components in addition to the above. Examples of such components include those generally used in a medium for stem cells, such as buffers, inorganic salts, antibiotics (e.g., one or more of the following: penicillin, kanamycin, streptomycin, etc.).

In the present specification, "% (w/v)" indicates a weight/volume percentage, and "% (v/v)" indicates a volume/volume percentage.

The epithelial cell sheet of the present invention can be produced in the same manner as in a known method for producing an epithelial sheet for use in COMET, except that the serum-free medium described above is used. Specifically, the method for producing an epithelial cell sheet of the present invention comprises culturing cells derived from oral mucosal epithelial cells on a substrate in the serum-free medium of the present invention.

In the method of the present invention, the culture is not performed in the presence of "feeder cells." In addition, no protein component, such as a serum component, is added to the medium.

The cells derived from the oral mucosal epithelium are cells that can be obtained from, for example, cells of an oral inner marginal mucosa epithelium part, a labial part, a palate part, and a buccal part. Preferably, the cells derived from the oral mucosal epithelium include oral mucosal epithelial stem cells and/or oral mucosal epithelial progenitor cells.

The cells derived from the oral mucosal epithelium may be cells derived from a subject into which the epithelial cell sheet is to be transplanted (autologous cells) or cells derived from other individuals (allogeneic cells). From the viewpoint of reducing rejection, autologous cells are preferable.

To remove impurities such as connective tissue, the cells derived from the oral mucosal epithelium are preferably subjected to a treatment with an enzyme such as dispase or trypsin, a filtration treatment, or the like.

The substrate is not particularly limited as long as it is a substrate that can be a substrate of an epithelial cell sheet. As the substrate, a membrane containing collagen as a main component can be used. In a preferred embodiment, the basement membrane is an amniotic membrane or denuded amniotic membrane. The denuded amniotic membrane is known and can be produced in accordance with, for example, the following document: Koizumi N et al. Invest Ophthalmol Vis Sci. 2000 August; 41(9):2506-13.

An epithelial cell sheet is formed on the substrate by culturing the cells derived from the oral mucosal epithelium on the substrate. It is preferable that the cells derived from the oral mucosal epithelium are seeded on the substrate so that, for example, the cell density is about $1\times10^3$ cells/cm$^2$ or more, preferably about $1\times10^3$ cells/cm$^2$ to $1\times10^7$ cells/cm$^2$, and more preferably about $1\times10^4$ cells/cm$^2$ to $1\times10^6$ cells/cm$^2$.

The culture can be performed, for example, using the serum-free medium described above by a technique known to a person skilled in the art. A preferred example of the technique of performing the culture is, but is not limited to, a technique of performing the culture at about 37° C. at a carbon dioxide concentration of about 5 to 10% (v/v). The culture under such conditions can be performed by using, for example, a known $CO_2$ incubator.

The culture period may be, for example, about 7 days to 3 weeks.

In order to obtain an epithelial cell sheet composed of a cell layer that is stratified, the culture method of the present invention preferably comprises temporarily exposing the uppermost surface of the cell layer to the outside of the medium. The uppermost surface of the cell layer can be temporarily exposed to the outside of the medium by, for example, temporarily removing a part of the medium or lifting the cell layer together with the basement membrane. The duration of time for bringing the uppermost surface of the cell layer into contact with air may be, for example, about 3 days to 2 weeks, preferably within 1 week, and more preferably within 3 days.

An epithelial cell sheet obtained by the culture method of the present invention can be used as a transplantation material for patients with intractable keratoconjunctival disease. Examples of intractable keratoconjunctival disease include diseases in which corneal epithelial stem cells become irreversibly dysfunctional or are lost, such as Stevens-Johnson syndrome, ocular pemphigoid, and alkaline erosion.

A specific example of the transplantation method is as follows. First, cicatricial tissue is incised in the corneal limbus of a patient with keratoconjunctival disease. Subsequently, cicatricial conjunctival tissue encroaching onto the cornea is removed, and the corneal stroma is exposed. Thereafter, a corneal epithelial sheet is sutured at a portion slightly inside the limbus. This method is similar to COMET, which has good treatment results, and the procedure is expected to be carried out in a highly stable manner.

In an epithelial cell sheet obtained by the culture method of the present invention, the expression of an epithelial stem cell marker (e.g., p75 neurotrophine receptor: p75NTR, CD271) and a proliferating cell marker (e.g., Ki76) can be detected as shown in the Examples described later; therefore, cells that maintain properties as stem cells are believed to be present. The expression of corneal epithelial cell markers (e.g., keratin 12 and keratin 3) can also be detected. Moreover, the gene expression patterns have a high degree of similarity to those in corneal epithelial cells compared with those in known epithelial cell sheets. An epithelial cell sheet obtained by the culture method of the present invention, which has these characteristics, is highly useful as a transplantation material for patients with intractable keratoconjunctival disease.

EXAMPLES

The present invention is described in more detail below with reference to Examples; however, the invention is not limited to these Examples.

1. Preparation of Cell Sheet
Material
Oral tissue was obtained from volunteer donors and as excess tissue derived from patients who had undergone oral surgery. All of the samples were treated within 1 to 2 hours after collection.
Culture
Oral mucosal epithelial cells were cultured according to a known method (Non-patent Literature 1 to 3).

Briefly, small oral mucosal biopsy was performed under local anesthesia. The obtained oral mucosal tissue was incubated at 4° C. for 5 hours with 1.2 IU dispase, followed by treatment with 0.05% (w/v) Trypsin-EDTA solution for 10 minutes to separate epithelial cells.

The obtained oral mucosal epithelial cells ($1\text{-}2\times10^5$ cells/ml) were seeded on a denuded amniotic membrane (AM) (amniotic membrane collagen sheet) spread on a culture insert.

The composition of the medium of the FFSF (feeder-free and serum-free) system according to the present invention was as described below.
FFSF (Feeder-Free and Serum-Free)
 Medium
Medium for Stem Cells
 Additive components
Recombinant human EGF (10 ng/ml) (Life Technologies)
Rho-associated protein kinase (ROCK) inhibitor Y-27632 (1 µl/ml) (Abcam Plc., Cambridge, Mass.)
B27 (2% (w/v)) (Life Technologies)
Hydrocortisone (1 µl/ml) (Lonza)
(−)-Epigallocatechin gallate (10 ng/ml) (Sigma-Aldrich, St. Louis, Mo.)
Dextran 40 (1% (w/v)) (Tokyo Kasei Kougyou, Tokyo)
Penicillin-Streptomycin (50 IU/ml) (Life Technologies)
As controls, culture was performed using the following compositions.
Control 1 (KSFM)
 Medium
Medium for stem cells: Defined K-SFM (Life Technologies)
 Additive components
Attached concomitant supplement
Control 2 (KGM+3T3 (control))
 Medium
Keratinocyte growth medium (KGM: ArBlast Co., Ltd., Kobe, Japan)
 Additive components
5% (w/v) FBS (fetal bovine serum) (Hyclone, Tauranga, New Zealand)
Feeder cells (co-culture)
NIH-3T3 fibroblasts (inactivated with mitomycin C (MMC))

FIG. 1 shows culture results (FIG. 1A-F) and schematic diagrams of culture schemas (FIG. 1G-I).

In phase-contrast microscope images, it was observed that colonies were formed on the denuded amniotic AM (denuded amniotic membrane) within 3 days after the start of the culture in all of the culture conditions. On day 7 after the start of the culture, a confluent primary culture of oral mucosal epithelial cells was formed that covered the whole AM (FIG. 1A-C). However, the morphology of the cells clearly differed between the KSFM and the control and between the KSFM and the FFSF. In the control and FFSF conditions, the oral mucosal epithelial cells exhibited a cobblestone-like morphology (FIG. 1B, C). On the other hand, in the KSFM conditions, elongated and enlarged cells were mainly observed (FIG. 1A).

After the culture for 2 weeks, in the control and FFSF conditions, a stratified structure comprising 4 to 5 layers was observed, differentiation sufficiently progressed (FIG. 1E, F), and a morphology similar to the corneal epithelium was observed. On the other hand, a single layer structure was only observed in the KSFM conditions (FIG. 1D).

The above results demonstrated the probability of the FFSF (feeder-free and serum-free) COMECS of the present invention that can be obtained as a stratified cell sheet.

2. Colony-Forming Efficiency

Regarding cells constituting the obtained epithelial cell sheets, the colony-forming efficiency (CFE) was evaluated.

Specifically, cells ($2 \times 10^3$) obtained in the control and FFSF culture conditions of Example 1 were seeded on 6-well plates (N=4). On day 7 of the culture, the cells were collected, fixed, and stained with 0.1% (w/v) truidine blue. The number of cells was counted independently by three researchers, and the average of the obtained data was determined.

Figure 2:
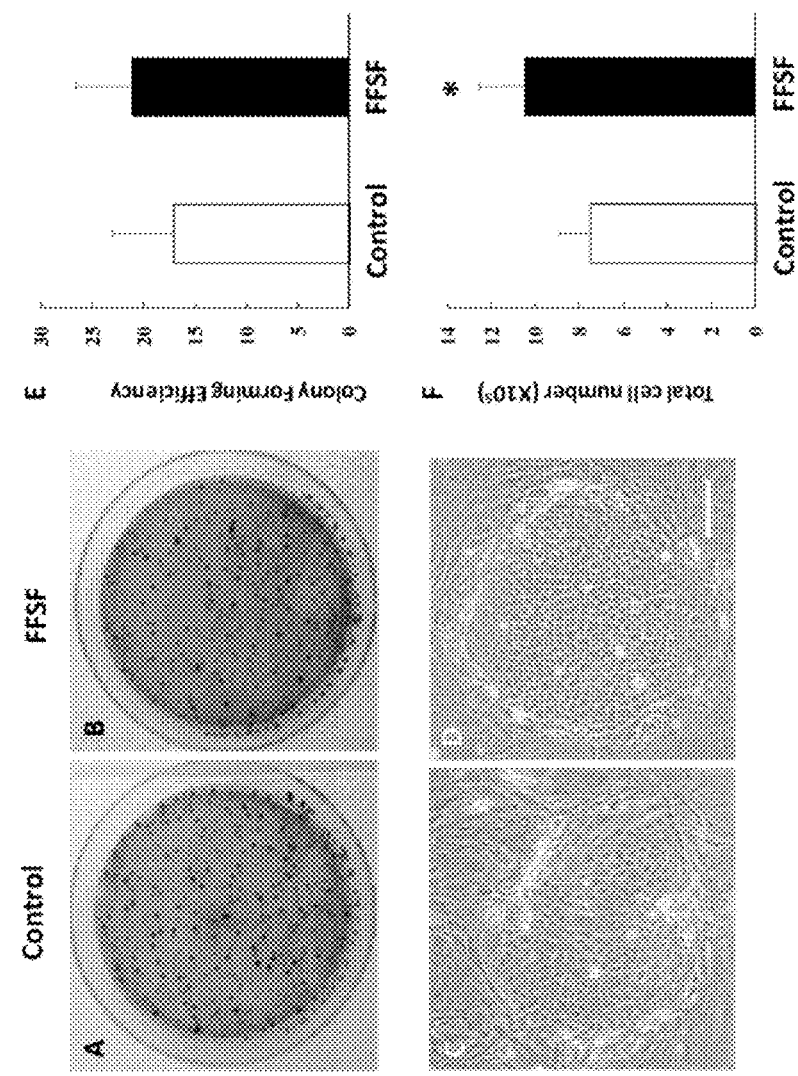
FIG. 2 shows evaluation results of colony-forming efficiency. (A-D): typical examples of colony-forming plates and phase-contrast microscope images of oral mucosal epithelial cells in the control and FFSF culture. (E): measurement results of colony-forming efficiency. (F): measurement results of the number of cells.

FIG. 2 shows the results. In phase-contrast microscope observation, ovoid and round cells were observed on day 7 of the culture (FIG. 2A-D). The CFE tended to be higher in the FFSF cells than in the control ($21.2 \pm 5.5\%$ vs $17.15 \pm 5.9\%$, N=4) (FIG. 2E). Further, the total number of cells in the case of using cells derived from the same donor was measured, and it was found that the total number of cells was larger in the FFSF than in the control ($10.5 \pm 2.1 \times 10^5$ vs $7.5 \pm 1.4 \times 10^5$, p<0.1, N=4) (FIG. 2F).

The above results revealed that the method of the present invention (FFSF culture system) enables the proliferative capacity of human oral mucosal epithelial cells to be maintained at a level at least similar or superior to the case of using conventional methods.

3. Transmission Electron Microscope Observation

The morphology of the obtained epithelial cell sheets was observed using a transmission electron microscope.

Figure 3:
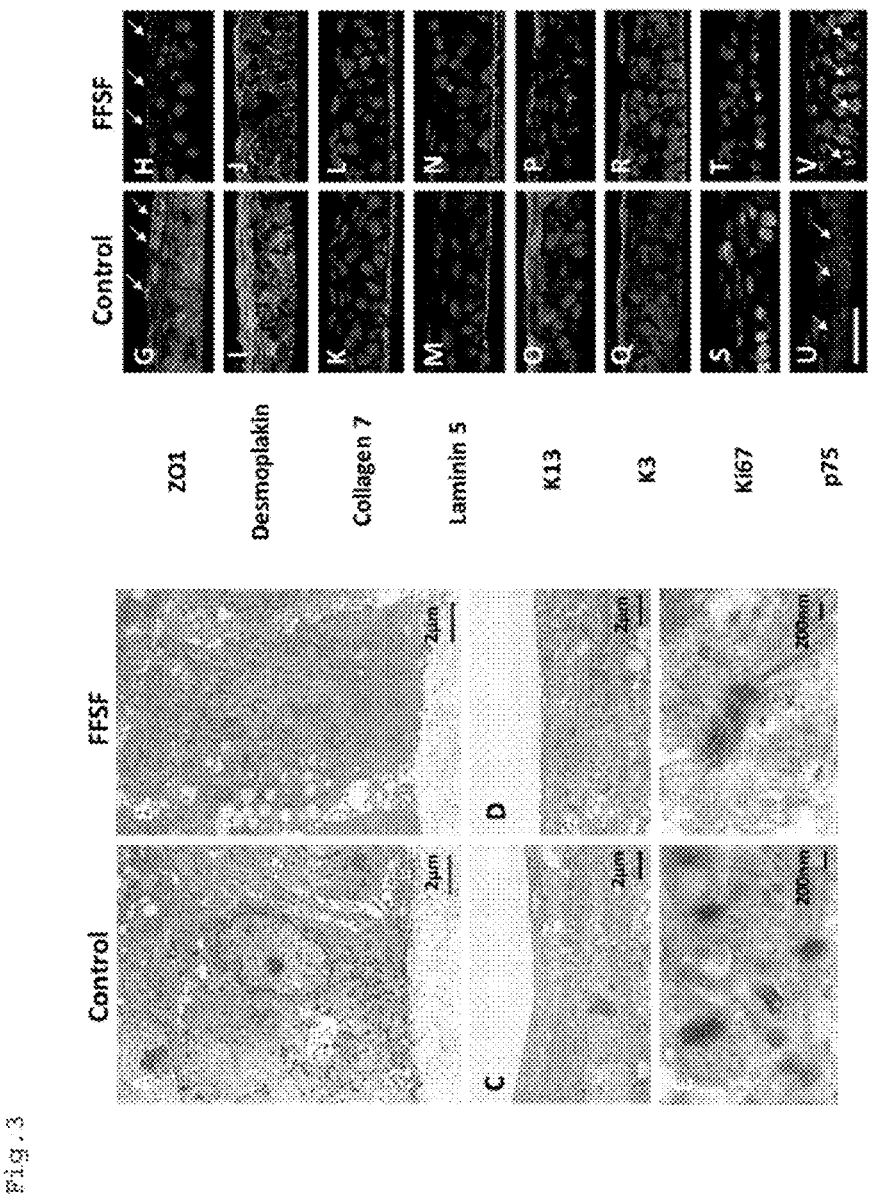
FIG. 3 shows morphological and cell biological features of a control COMECS and an FFSF COMECS. (A-F): transmission electron microscope images; and (G-V): antibody stain images. Nuclei were stained with propidium iodide (PI). Bar: 50 μm.

FIG. 3A-F shows the results. In both the control and FFSF COMECSs, the cells were healthy, and differentiation into basal columnar cells, suprabasal cuboid wing cells, and flat squamous superficial cells was confirmed (FIG. 3A-D). In all cell layers, oral mucosal epithelial cells were closely attached to neighboring cells via numerous desmosomes (FIG. 3E, F).

4. Antibody Staining

Antibody staining of various markers was performed for the obtained epithelial cell sheets.

FIG. 3G-V shows results of co-staining with propidium iodide (nuclear staining). In both the control and FFSF COMECSs, ZO-1, which is a tight-junction-related factor, in apical cells (FIG. 3G, H; arrows); desmoplakin, which is a cell-cell adhesion factor (FIG. 3I, J); collagen 7 and laminin 5, which are basement membrane constituent factors, in the basement membrane (FIG. 3K-N); oral mucosal epithelium-specific keratin 13 (K13) and cornea-specific keratin 3 (K3) (FIG. 3O-R); Ki67, which is a marker of cells undergoing active cell proliferation (FIG. 3S, T); and p75, which is an oral mucosal epithelial stem cell/progenitor cell marker (FIG. 3U, V), were confirmed.

Thus, the FFSF COMECS has a cell junction, basement membrane constituent protein, differentiation capacity, proliferative capacity, and stem cell potential, which are considered to be essential for clinical adaptation and application.

5. Gene Expression Analysis

Expression analysis of the following genes was performed by the RT-PCR method.

TABLE 1

| | |
|---|---|
| Keratin 12 (K12) | corneal epithelial cell marker |
| Keratin 3 (K3) | corneal epithelial cell marker |
| ALDH3 | corneal epithelial cell marker |
| TKT | corneal epithelial cell marker |
| p75 | stem cell/progenitor cell marker |
| HPRT | housekeeping gene (control) |

The primers used are as follows.

TABLE 2

| Sequences for PCR | | |
|---|---|---|
| human K12 | F | AATCATGGGGCAGATCTTGT (SEQ ID NO: 1) |
| | R | AAGGTGATGGTTTGGAGGAA (SEQ ID NO: 2) |
| human K3 | F | GGCAGAGATCGAGGGTGTC (SEQ ID NO: 3) |
| | R | GTCATCCTTCGCCTGCTGTAG (SEQ ID NO: 4) |
| human ALDH3 | F | TTGCAGAGACATCCAGTGGT (SEQ ID NO: 5) |
| | R | TTGGTCTAGAAAGGGGTGGA (SEQ ID NO: 6) |
| human TKT | F | CTGCTTCATCCGGACCAG (SEQ ID NO: 7) |
| | R | CACACTTCATACCCGCCCTA (SEQ ID NO: 8) |
| human p75 | F | TGAGTGCTGCAAAGCCTGCAA (SEQ ID NO: 9) |
| | R | TCTCATCCTGGTAGTAGCCGT (SEQ ID NO: 10) |
| human β-actin | F | GGACTTCGAGCAAGAGATGG (SEQ ID NO: 11) |
| | R | ATCTGCTGGAAGGTGGACAG (SEQ ID NO: 12) |

F: Forward, R: Reverse

Figure 4:
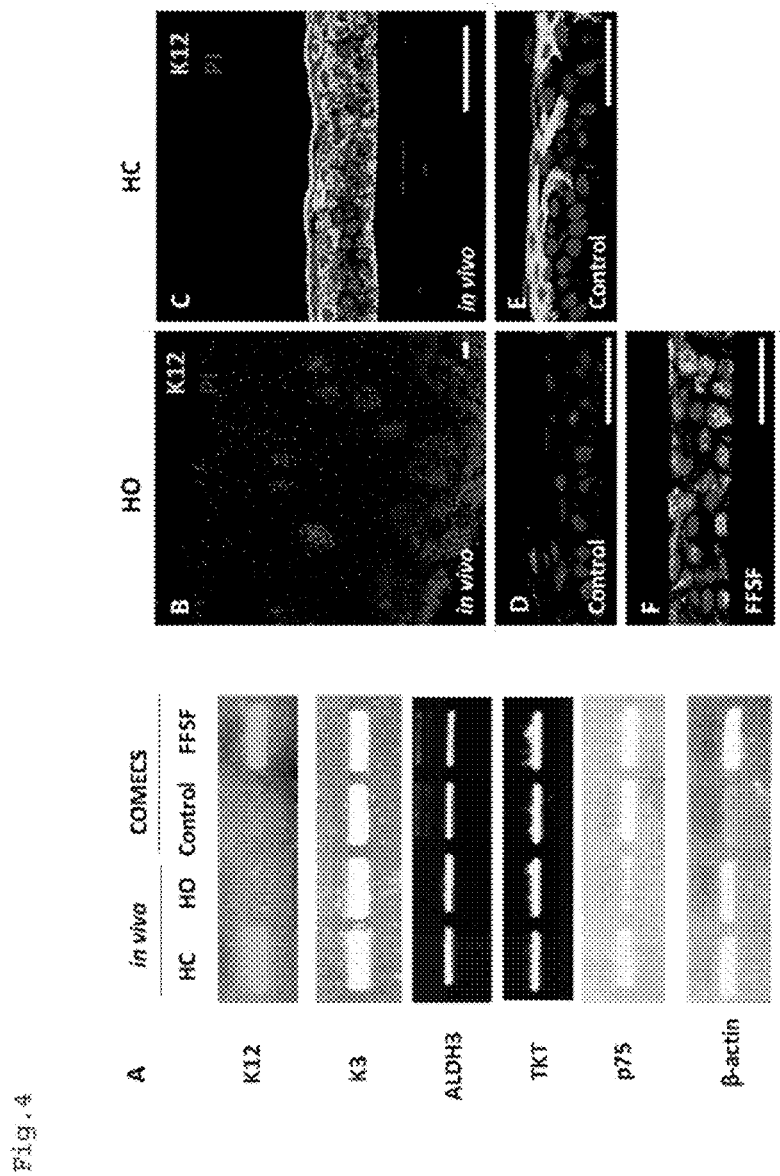
FIG. 4 shows results of analysis of cornea-specific marker expression in the FFSF COMECS. (A): PCR results; (B-F): results of antibody staining of K12, co-staining with propidium iodide (PI). (B): human oral mucosal epithelium in vivo (human oral mucosa (HO)); (C): human corneal epithelium in vivo (human cornea (HC)); (D): control COMECS; (E): cultivated corneal epithelial cell sheet; and (F): FFSF COMECS. Bar: 50 μm.

FIG. 4A shows the results. Among corneal epithelial markers, K12 is highly reliable as a specific marker. Other corneal epithelial markers include K3, ALDH3, and TKT. The expression of K12 was detected in the FFSF COMECS, whereas the expression of K12 was not detected in the control COMECS. On the other hand, K3, ALDH3, and TKT, which are corneal epithelial markers, and p75, which is a stem cell/progenitor cell marker, were detected in both.

Subsequently, the results of RT-PCR were verified by an antibody staining method.

FIG. 4B-E shows the results. It was revealed that neither human oral mucosal epithelial cells (in vivo) nor the control COMECS expressed K12 (FIG. 4B, C), whereas local and sporadic expression of K12 was observed in the FFSF COMECS (FIG. 4F).

The expression pattern of K12 in the FFSF COMECS may differ from those in the corneal epithelium (in vivo) and a cultivated corneal epithelial cell sheet obtained by a conventional method (control) (FIG. 4C, E).

6. Clonal Analysis

Clonal analysis of the epithelial cell sheet obtained by the method of the present invention was performed. The analysis was carried out in accordance with the following document: Barrandon Y, Green H. Proceedings of the National Academy of Sciences of the United States of America, 1987; 84:2302-2306.

Figure 5:
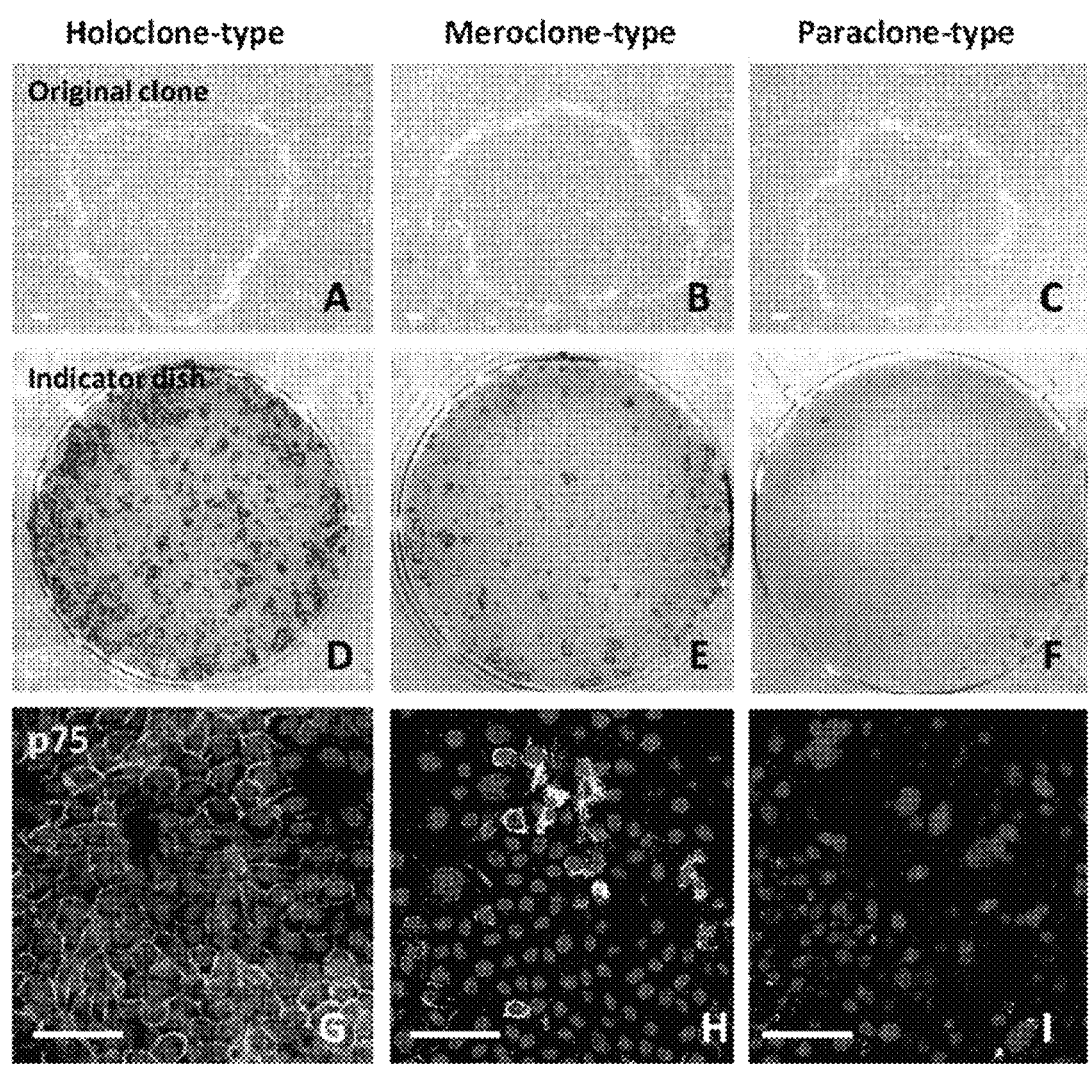
FIG. 5 shows results of clonal analysis. (A): original clone of the holoclone type; (B): original clone of the meroclone type; (C): original clone of the paraclone type. (D): indicator dish of the holoclone type; (E): indicator dish of the meroclone type; (F): indicator dish of the paraclone type. (G): immunostaining for p75 of the holoclone type; (H): immunostaining for p75 of the meroclone type; and (I): immunostaining for p75 of the paraclone type.

FIG. 5 shows the results. Typical original clones of holoclones are large, have a smooth perimeter, and contain mainly small cells. On plates, holoclones formed large, rapidly growing colonies, and not more than 5% of the cells differentiated terminally (FIG. 5A, D). Typical original clones of paraclones are small and contain mainly large differentiated cells. On plates, paraclones formed either no colonies or uniformly small, terminal colonies (FIG. 5C, F). Meroclones exhibit properties that are intermediate between holoclones and paraclones. On plates, meroclones formed both colonies that grew and colonies that did not grow (FIG. 5B, E). 23.6±12.5% were holoclones, 34.9±10.5% were meroclones, and 41.5±11.3% were paraclones. This indicates that holoclone-type, meroclone-type, and paraclone-type cells, which are identified in skin and ocular surfaces, constitute the proliferative compartment of the FFSF COMECS.

Immunohistochemical analysis was performed to investigate expression of p75 in these clonal types. The results showed that strong expression of p75 was confirmed in the cell membrane of holoclone-type cells (FIG. 5G), moderate expression of p75 was confirmed in the cell membrane of some of the small cells of meroclone-type cells (FIG. 5H), and the expression of p75 was rarely confirmed in paraclone-type cells (FIG. 5I).

These results revealed that a COMECS containing holoclone-type stem cells that express p75 at high levels can be obtained by the method of the present invention.

7. Xenotransplantation of COMECS

A prepared epithelial cell sheet was xenotransplanted into albino rabbits (2 to 2.5 kg) in accordance with the following document: Kobayashi M, Nakamura T, Yasuda M et al. Stem cells translational medicine, 2015; 4:99-109.

Figure 6:
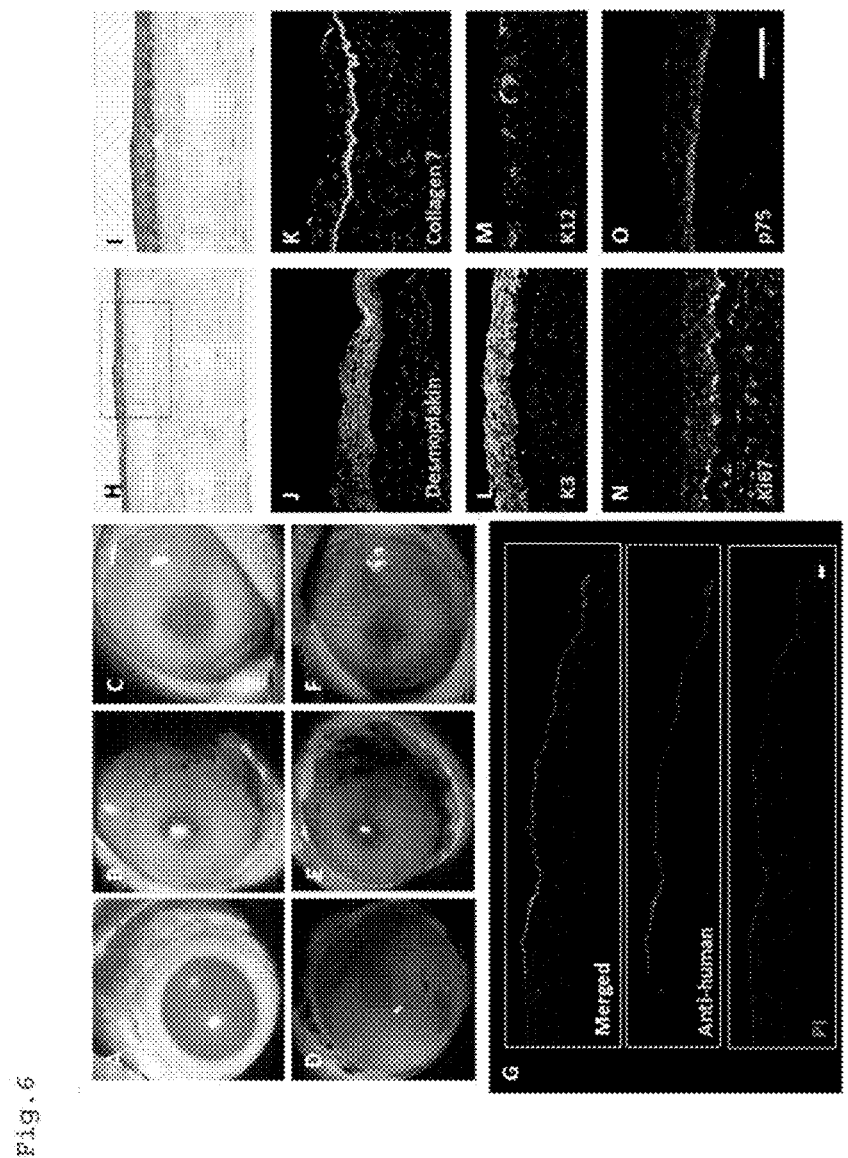
FIG. 6 shows results of xenotransplantation of a COMECS. (A, D): slit-lamp photographs of a rabbit eye before transplantation, with and without fluorescein treatment; (B, E): slit-lamp photographs of a rabbit eye on day 7 after transplantation, with and without fluorescein treatment; (C, F): slit-lamp photographs of a rabbit eye on day 14 after transplantation, with and without fluorescein treatment. (G): staining with anti-human nucleus antibodies at a transplanted area. (H, I): HE staining. Antibody staining for (J): desmoplakin, (K): collagen 7, (L): keratin 3 (K3), (M): keratin 12 (K12), (N): Ki76, and (O): p76. Nuclei were co-stained with propidium iodide. Bar: 100 μm.

FIG. 6 shows the results.

Before the surgery, corneal epithelial cells including the limbal region were totally removed (FIG. 6A). Fluorescein staining confirmed that the corneal epithelial cells were completely removed (FIG. 6D).

The human FFSF COMECS of the present invention was transplanted onto the corneal surfaces and fixed with a 10-0 nylon suture (N=3). 7 days and again 2 weeks after the transplantation surgery, the corneal surfaces of all of the treated eyeballs into which the human FFSF COMECS was transplanted were confirmed to be clear and smooth with no excessive postoperative inflammation (FIG. 6B, C). Fluorescein staining confirmed that the whole cornea was covered with the xenogeneic COMECS (FIG. 6E, F).

Histological examination on day 14 after the surgery confirmed that the transplanted COMECS was attached well to the host tissue, with no subepithelial cell infiltration (FIG. 6H, I). Hematoxylin-eosin staining confirmed that the transplanted COMECS contained well-stratified differentiated cells (FIG. 6H, I). Staining with anti-human nucleus antibodies confirmed the presence of the transplanted human COMECS (FIG. 6G).

The expression patterns of multiple cell markers in the transplanted COMECS were also examined. Desmoplakin was found to be expressed in the cell membrane (FIG. 6J), and collagen 7, which is a basement membrane constituent protein, was found to be expressed (FIG. 6K). Keratin 3 (K3) was clearly expressed in all transplanted COMECSs, and keratin 12 (K12) was sporadically expressed in the transplanted areas (FIG. 6L, M). The expression of Ki67 and p75 was confirmed in the basal layer of the transplanted COMECS (FIG. 6N, O). These results revealed that the transplanted cells maintain proliferative capacity and properties as stem cells/progenitor cells on the rabbit corneal surfaces and that the prepared FFSF COMECS can be applied well to in vivo environments and maintain visual function well also after surgery.

8. Gene Expression Profile Analysis

Regarding the epithelial cell sheet (FFSF COMECS) of the present invention, control epithelial cell sheet (control COMECS), corneal epithelium (HC in vivo), and oral mucosal epithelium (HO in vivo), total RNA was extracted, cDNA was prepared, and analysis of gene expression profiles was performed using GeneChip Human Genome U133 Plus 2.0 (Affymetrix, Santa Clara, Calif.). Array data analysis was performed with Affymetrix GeneChip operating software (GCOS) version 1.0.

Figure 7:
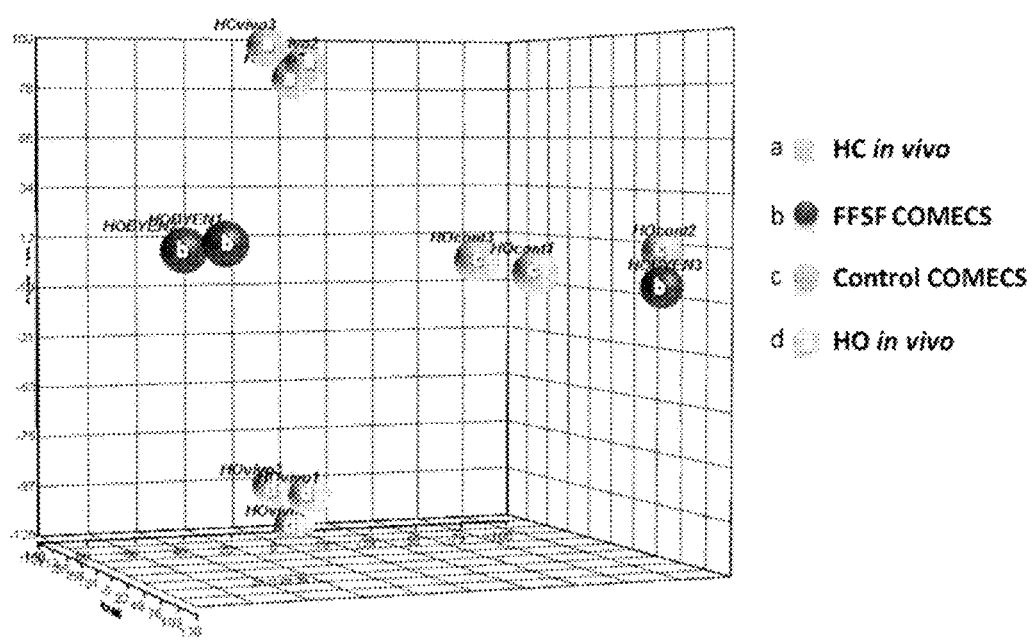
FIG. 7 shows a gene expression profile of the FFSF COMECS by principal component analysis (PCA).
Figure 8:
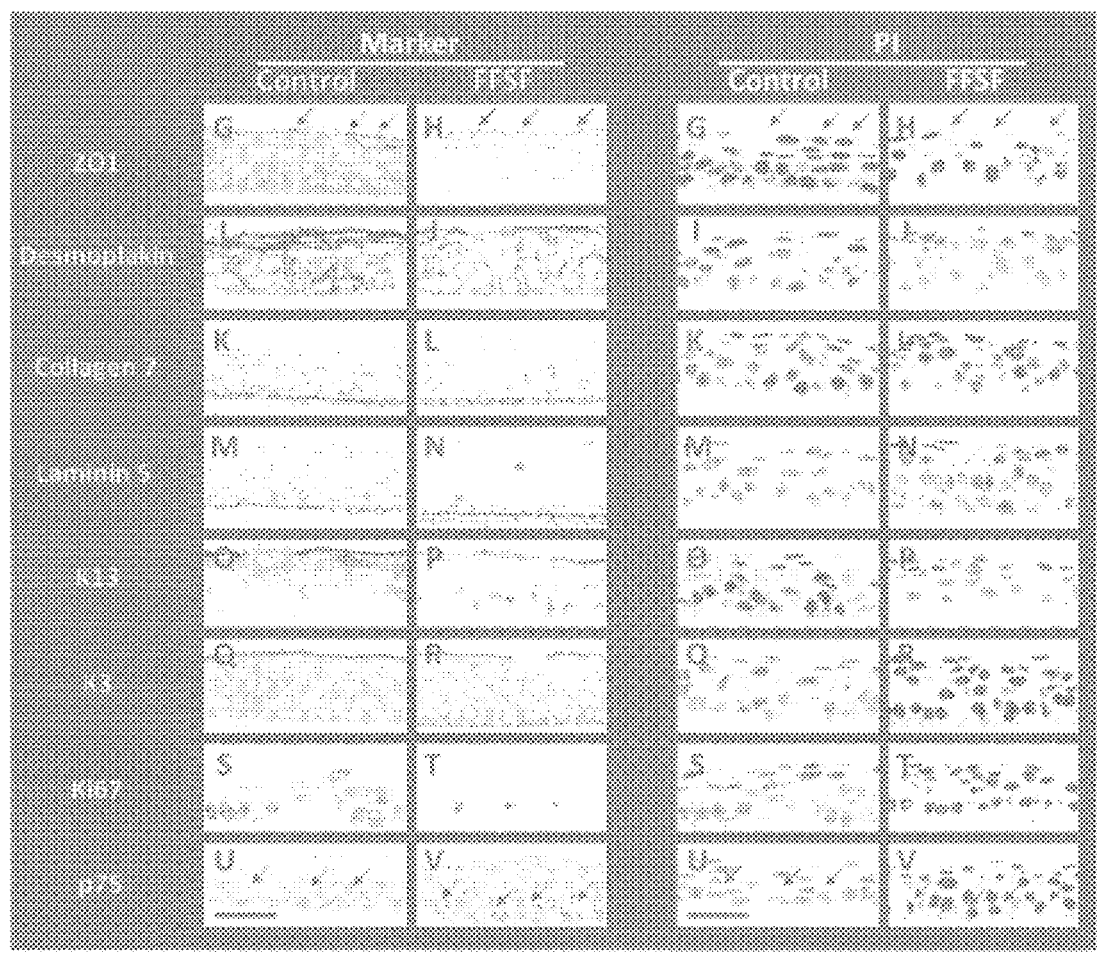
FIG. 8 shows black and white inverted images of FIG. 3G-V.
Figure 9:
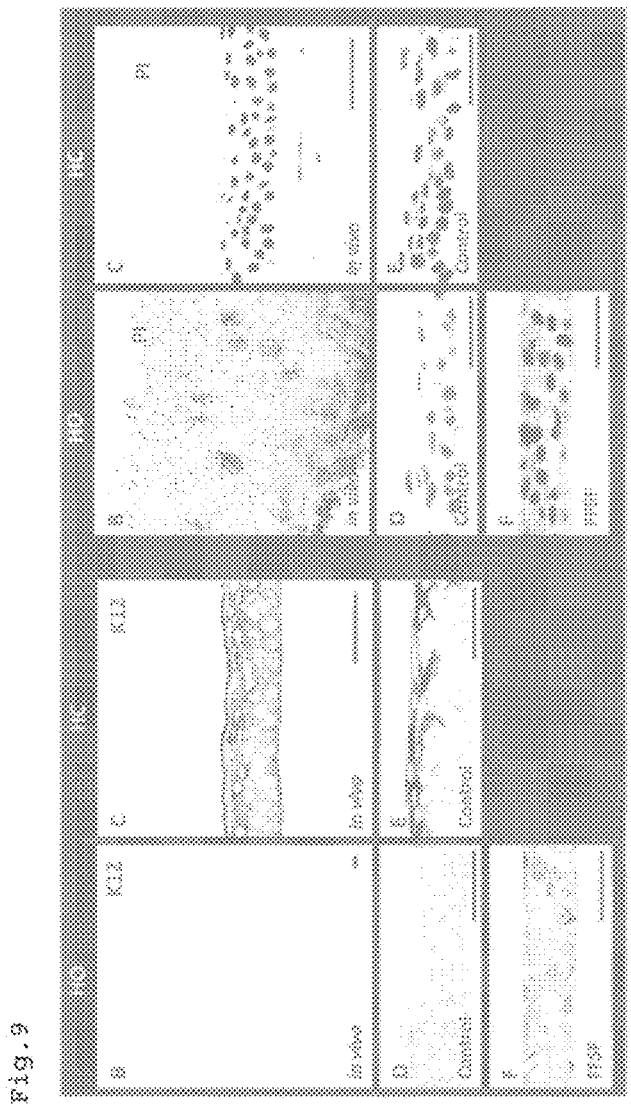
FIG. 9 shows black and white inverted images of FIG. 4B-F.
Figure 10:
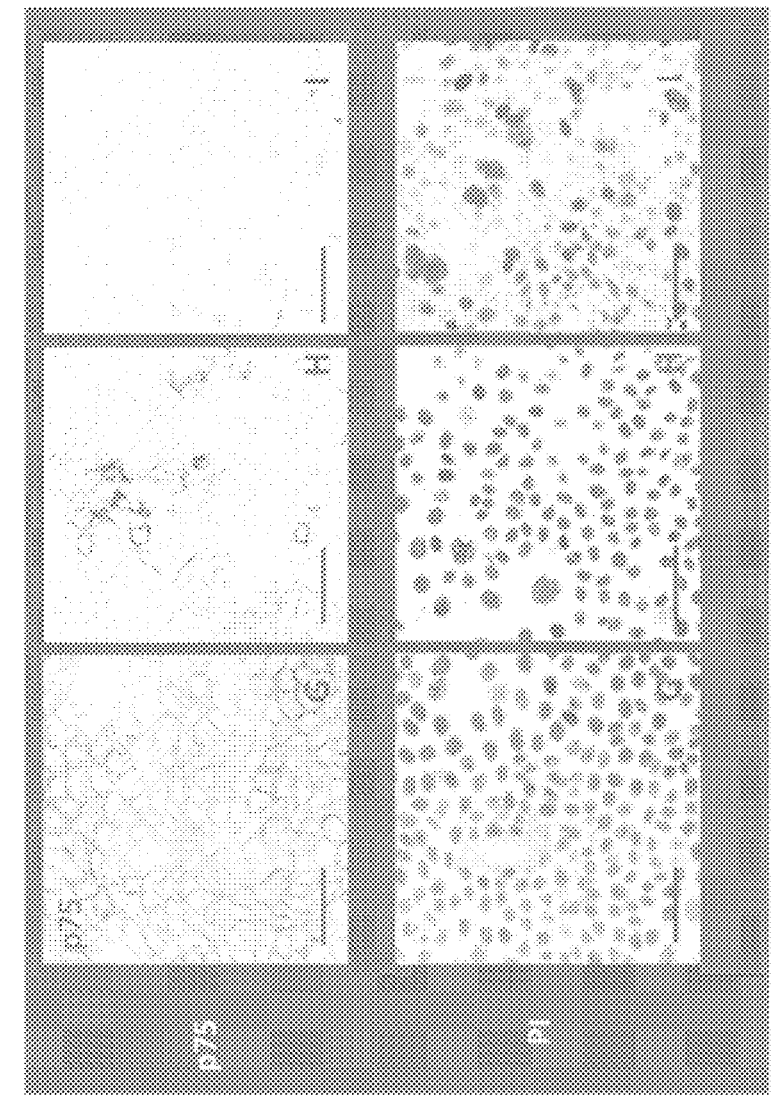
FIG. 10 shows black and white inverted images of FIG. 5G-I.
Figure 11:
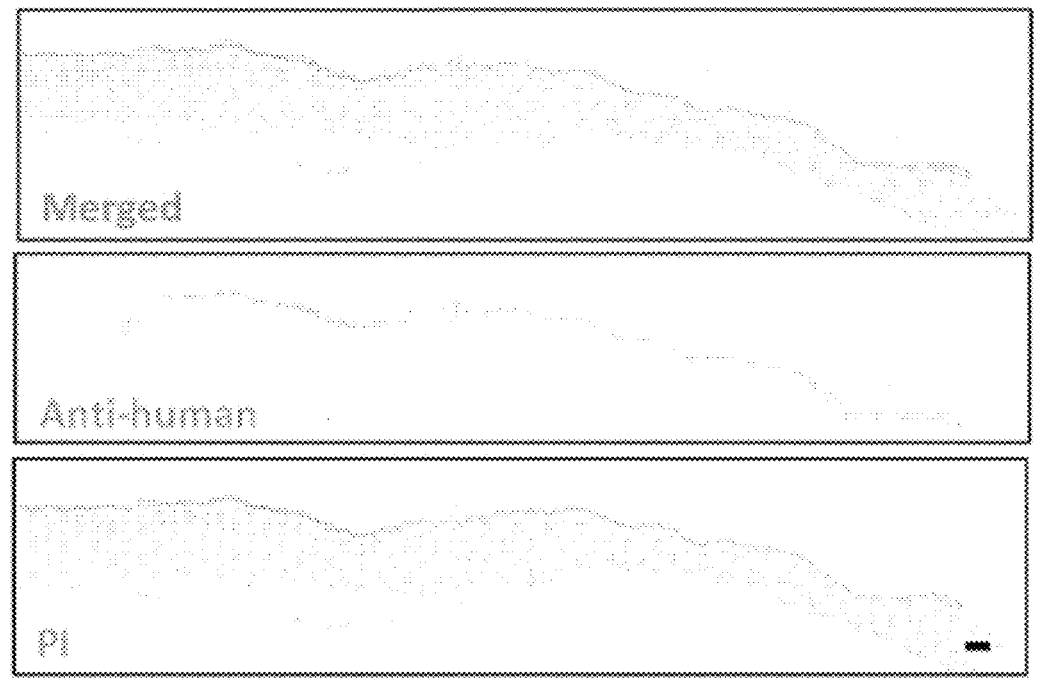
FIG. 11 shows black and white inverted images of FIG. 6G.

FIG. 7 shows results of principal component analysis (PCA) mapping. The results revealed that the gene expression profile of the human corneal epithelium in vivo was quite different from that of the human oral mucosal epithelium in vivo. The gene expression profiles of both the epithelial cell sheet (FFSF COMECS) of the present invention and the control epithelial cell sheet (control COMECS) were intermediate between the human corneal epithelium and the human oral mucosal epithelium. The gene expression profile of the FFSF COMECS tended to be closer to that of the human corneal epithelium than that of the control COMECS. This result suggests that the method of the present invention influences the integrity and characteristics of epithelial cells.

The invention claimed is:

1. A method for producing an epithelial cell sheet in which cells that express an epithelial stem cell marker, a proliferating cell marker, and corneal epithelial cell marker keratin 12 and maintain a property as stem cells are present, the method comprising culturing cells derived from oral mucosal epithelium on a substrate in a serum-free medium, wherein the serum-free medium comprises
   (i) EGF protein or KGF protein,
   (ii) a serum-free supplement comprising biotin, L-carnitine, corticosterone, ethanolamine, D(+) galactose, reduced glutathione, linoleic acid, linolenic acid, progesterone, putrescine, retinyl acetate, selenium, triiodo-L-thyronine, vitamin E, vitamin E acetate, bovine albumin, catalase, insulin, superoxide dismutase, and transferrin,
   (iii) a ROCK inhibitor, and
   (iv) one or more catechin.

2. The method according to claim 1, wherein the medium further comprises at least one member selected from the group consisting of
   (v) polysaccharides, and
   (vi) corticoids.

* * * * *